United States Patent [19]

Bellasio

[11] 4,385,179

[45] May 24, 1983

[54] PROCESS FOR PREPARING N-PYRROLYL-PYRIDAZINEAMINE DERIVATIVES

[75] Inventor: Elvio Bellasio, Como, Italy

[73] Assignee: Gruppo Lepetit S.p.A., Milan, Italy

[21] Appl. No.: 332,272

[22] Filed: Dec. 18, 1981

[30] Foreign Application Priority Data

Dec. 22, 1980 [IT] Italy ............................. 26846 A/80

[51] Int. Cl.$^3$ ............................................ C07D 413/14
[52] U.S. Cl. ..................................... 544/111; 544/60; 544/237; 544/238; 542/417
[58] Field of Search .................. 544/111, 237, 238, 60

[56] References Cited

FOREIGN PATENT DOCUMENTS 9655 4/1980 European Pat. Off.
1373548 11/1974 United Kingdom.

OTHER PUBLICATIONS

Pifferi et al., J. Med. Chem. (1975) vol. 18, No. 7, pp. 741-746.

Castle, Pyridazines, John Wiley (1973), pp. 463-469 & 635-637.
Castle, Condensed Pyridazines Including Cinnolines and Phthalazines, John Wiley (1973), pp. 560-571 & 596-599.

Primary Examiner—Henry R. Jiles
Assistant Examiner—Bernard Dentz
Attorney, Agent, or Firm—William J. Stein; Gary D. Street; Raymond A. McDonald

[57] ABSTRACT

The present invention refers to a new process for preparing N-2,3,4,5-substituted-1H-pyrrol-1-yl)-6-substituted amino-3-pyridazineamine, known as antihypertensive agents. The process is characterized in that a suitable 3,6-dihalogenopyridazine is reacted with hydrazine hydrate or other hydrazine derivatives of formula $NH_2$ NHR, the obtained compound is reacted with a suitable dicarbonyl compound yielding first an alcandione-bis-[6-halogen-3-pyridazininyl]hydrazone, and then a 6-halogen-3-pyrrolylpyridazineamine derivative which is in turn reacted with an amine to yield the desired compounds.

9 Claims, No Drawings

PROCESS FOR PREPARING N-PYRROLYL-PYRIDAZINEAMINE DERIVATIVES

The present invention refers to a new process for preparing compounds of general formula I

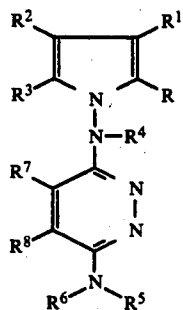

and their acid addition salts, wherein the symbols R, $R^1$, $R^2$, and $R^3$ may be the same or different and are independently selected from hydrogen and $(C_1-C_4)$alkyl, $R^4$ represents hydrogen, $(C_1-C_4)$alkyl, mono- or di-$(C_1-C_4)$alkylamino$(C_1-C_4)$alkyl, halogen$(C_1-C_4)$alkanoyl, carbo$(C_1-C_4)$alkoxy, carbobenzyloxy, $R^5$ and $R^6$ independently represent hydrogen, $(C_1-C_6)$alkyl, $(C_3-C_6)$alkenyl, $(C_3-C_6)$alkynyl, hydroxy$(C_1-C_6)$alkyl, $(C_1-C_4)$alkoxy$(C_1-C_6)$-alkyl, $(C_2-C_6)$alkanoyloxy$(C_1-C_6)$alkyl, phenyl or phenyl$(C_1-C_4)$alkyl, wherein the phenyl group may optionally be substituted with 1 to 3 substituents independently selected from chloro, bromo, fluoro, $(C_1-C_4)$alkyl, and $(C_1-C_4)$alkoxy, hydroxy and hydroxy$(C_1-C_4)$alkyl, or with a methylenedioxy group, or $R^5$ and $R^6$ taken together with the adjacent nitrogen atom represent a fully or partially hydrogenated 5 to 7 membered heterocyclic ring which may contain a further heteroatom selected from O, N, and S and optionally bear 1 or 2 substituents selected from $(C_1-C_4)$alkyl, hydroxy, hydroxy$(C_1-C_4)$alkyl, $(C_1-C_4)$alkoxy, phenyl which may optionally be substituted with 1 to 3 substituents independently selected from chloro, fluoro, bromo, hydroxy$(C_1-C_4)$alkyl and $(C_1-C_4)$alkoxy, $R^7$ and $R^8$ represent hydrogen atoms or, taken together, a 1,3-butadienylene group forming a benzo system fused with the pyridazine ring.

The process of the present invention, which is outlined in Scheme 1, is a multi-step process which essentially comprises the reaction of a 3,6-dihalogenopyridazine wherein $R^7$ and $R^8$ are as above, with hydrazine hydrate or a hydrazine derivative of formula $NH_2$—NHR followed by the reaction of the obtained compounds of formula III with a suitably selected dicarbonyl compound of formula IV, and finally, the reaction of the obtained 6-halo-N-pyrrolyl-3-pyridazineamine with the amine of formula $NHR^5R^6$ to yield the desired compound of formula I.

SCHEME 1

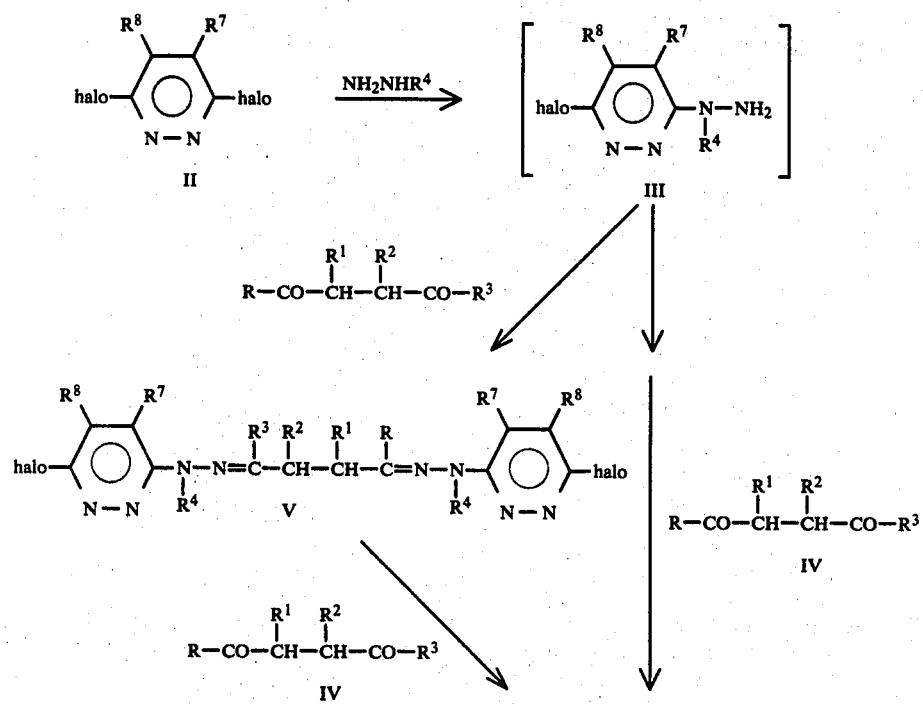

SCHEME 1

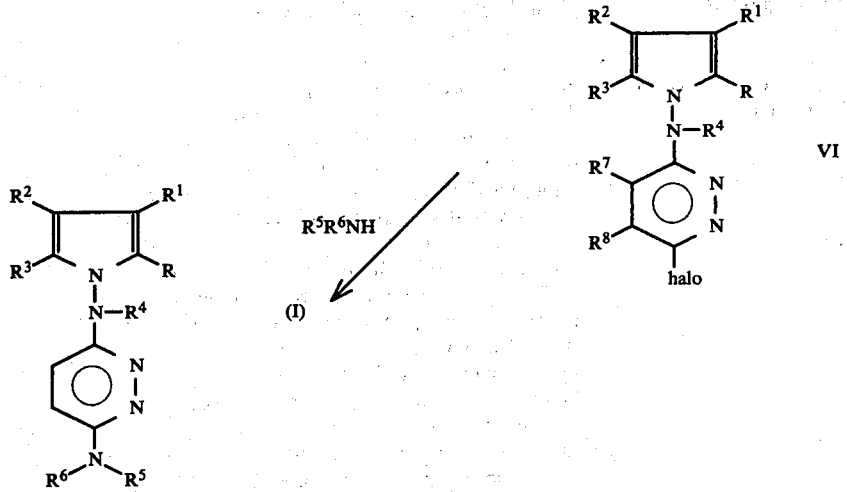

N-pyrrolyl pyridazineamines of formula I are known from European Patent Application Publication No. 9655 as antihypertensive agents.

According to said application the compounds of formula I are prepared reacting a 3-hydrazino-6-substituted aminopyridazine derivative with at least an equimolecular amount of a dicarbonyl compound of formula

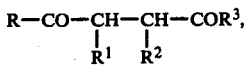

wherein R, $R^1$, $R^2$ and $R^3$ have the above meanings. In the same application, it is taught that the compounds of formula IX are obtained according to the procedure described in literature, citing in particular, U.K. Pat. Nos. 1,157,642, 1,373,548, and 1,299,421; Bellasio et al., Il Farmaco Ed. Sci. 24, 924, (1969) and Pifferi et al., Journal of Medicinal Chemistry, 18, 741, (1975). These procedures are summarized in Scheme 2 below:

SCHEME 2

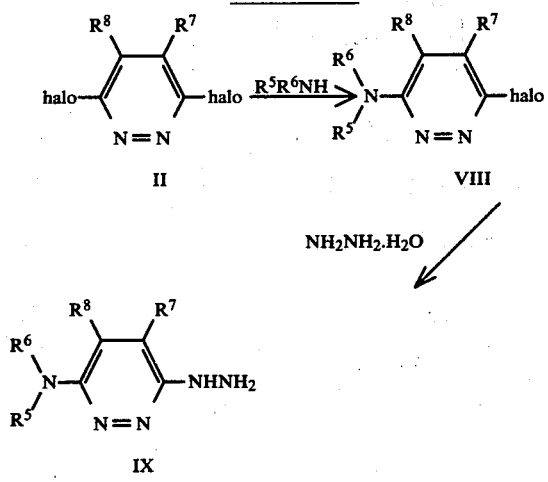

The 3,6-dihalogen pyridazine derivatives of formula II wherein $R^7$ and $R^8$ have the above meanings, and halo stands for chloro, bromo or iodo, is reacted with a double molar amount of the suitable amine of formula $R^5R^6NH$, wherein $R^5$ and $R^6$ are as above, to yield the compound of formula VIII. The 3-halogen-6-pyridazineamine derivative so obtained is then reacted with an excess of 98% hydrazine hydrate yielding the hydrazine derivative of formula IX.

Following the reaction pathway outlined in the above Scheme 2, a certain number of hydrazine pyridazineamines can be prepared. It was noticed, however, that the reactivity toward the nucleophilic substitution of the halogen atom, in the compounds of formula VIII, decreases when the basicity of the $R^5R^6N$—group increases. As a consequence, the yields in compounds IX decreases when the $R^5R^6N$—group is a strong electron-donating group, and, accordingly the number of derivatives that can conveniently be prepared by these procedures is limited.

Moreover, the above quoted literature together with Belgian Pat. Nos. 744,286 and 744,686, and Dutch patent application No. 7009434, clearly point out that the skilled man, faced with the problem of the synthesis of 6-hydrazino-3-pyridazineamines has always preferred to introduce first the amine group and then the hydrazine group onto the pyridazine ring. Some attempts made in our laboratories to invert the order of introduction of the reactants, i.e. to introduce first the hydrazine group and then the amine group, failed, since the 3-halogen-6-pyridazinylhydrazine did not react with an amine even under high pressure or at high temperatures. In addition, the hydrazine derivative of formula IX is generally separated with difficulty, so many times the yields are lower than expected and, accordingly, the number of derivatives that can conveniently be prepared is limited.

The process of the present invention, which follows a new pathway according to which hydrazine is introduced onto the pyridazine ring before the introduction of the amine group, affords the compounds of formula I in unexpectedly much higher yields than those afforded by the methods outlined in European patent application Publication No. 9655. Moreover, the process of the present invention is much more flexible and safer. In fact, while the overall yields in N-pyrrolylpiridazineamine, starting from suitable 3,6-dihalogenpyridazine according to the prior-art methods range between 5% and 30%, the overall yields following the present process are more than doubled and in any case higher than 30%.

As stated above, another advantage is the increased flexibility of this process. In fact a variety of amino derivatives of formula $R^5R^6NH$ can be easily employed in the last reaction step, irrespective of their basicity, while the prior-art processes, showed reduced yields for the increasing basicity of the $-NR^5R^6$ group (see above). A further advantage is that the present process is safer than those previously described, since the first step of introducing a hydrazine group onto the pyridazine ring of a 3,6-dihalogenpyridazine, requires moderate concentrations of hydrazine hydrate (about 5%-25%), that are well below the 40% value which may be considered the threshold value at which the hazards of using highly concentrated hydrazine reactants become significant. On the contrary, the prior-art processes, describe the use of highly concentrated hydrazine hydrate (about 98%).

At this concentration, evidently, all the risks and drawbacks described for example in Merck Index 8th Edition p.539 are highly significant.

As outlined in Scheme 1 the first step of the process of the present invention, comprises the reaction of the selected 3,6-dihalogenpyridazine with hydrazine hydrate. As stated above, the hydrazine hydrate is preferably 5-25% hydrazine hydrate. This reaction step, is carried out in the presence of a basic agent which acts as a hydrogen halide acceptor without adversely interfering with the reactants or the products of the reaction. According to a preferred embodiment, the basic agent is employed in an equimolecular amount or preferably in excess over the pyridazine derivative of formula II. Examples of such agents are alkali metal or earth alkali metal carbonates, bicarbonates, and hydroxides. The reaction mixture is generally heated to a temperature between 60° C. and the reflux temperature, and, preferably, to the reflux temperature.

Sometimes, an organic solvent is added in order to facilitate the dissolution of the reaction mixture and then, it is removed in vacuo before starting the reaction. The reaction time is generally 3-24 hours. Once the reaction is completed, water is added and to save time, the temperature is kept higher than 60° C. in order to avoid the precipitation of the halogen pyridazinyl hydrazine of formula III, while a half-molar amount or, preferably, a slight excess of the dicarbonyl compound of formula IV is, in turn, added. After said addition, a compound of formula V precipitates, and is collected and washed according to the usual procedures.

In order to complete the precipitation, it is useful to neutralize the solution with a mineral acid preferably a hydrohalide acid, before collecting the precipitate. To do this, 17% hydrochloric acid has been found particularly useful.

In the second step of the process of the invention, the intermediate of formula V is reacted with a further amount of the dicarbonyl compound IV to yield the 6-halo-N-pyrrolyl-3-pyridazineamine of formula VI. The reaction is preferably carried out adding the intermediate V to a mixture of an equimolar amount of the dicarbonyl compound VI and an acid catalyst in a suitable organic solvent, while heating to the reflux temperature. Solvents which may suitably be employed are for instance, lower alkanoic acids and their $(C_1-C_4)$alkyl esters, benzene, toluene, tetrahydrofuran, dioxane, and the like, and mixture thereof.

Although several types of acidic catalysts such as hydrohalic acids, sulfuric acid, p-toluenesolfonic acid and Lewis acids may be employed, lower alkanoic acids are particularly suitable since they may be used simultaneously as the reaction solvents and catalysts. Among the lower alkanoic acids, acetic acid is preferred. Once the addition is completed, the intermediate of formula VI precipitates and is recovered by filtration and purified, if necessary, by means of the usual procedures.

Alternatively, depending on the solubility of the intermediate of formula V in the solvent system employed, the formation of the 6-halo-3-pyrrolyl-pyridazineamine of formula VI from the intermediate 6-halo-3-hydrazinopyridazine of formula III can be achieved in one step, by adding directly to the intermediate III a molar proportion, or a slight excess, of the dicarbonyl compound of formula VI.

Also in this case, the obtained compound of formula VI is recovered by filtration and purified, if desired, according to usual procedures.

Finally, the 6-halo-N-pyrrolyl-3-pyridazineamine intermediate of formula VI is converted into the desired compound of formula I by reaction with a suitably selected amine of formula $R^5R^6NH$, preferably in the presence of a small quantity of an acid addition salt of the amine, that acts as a catalyst in the nucleophilic substitution. Particularly useful salts are the hydrohalides, such as hydrochloride, hydrobromide, and hydroiodide.

This reaction step can be carried out in the presence of suitable organic solvents such as alkanols containing from 3 to 6 carbon atoms, for instance, propanol, butanol, isobutanol, 1-pentanol, 2-pentanol, 3-pentanol, 3-methyl-2-pentanol, 4-methyl-3-pentanol, 1-hexanol, 2-hexanol, or 3-hexanol, cycloalkanols containing from 5 to 7 carbon atoms, e.g. cyclopentanol, cyclohexanol, or cycloheptanol, glycols containing from 2 to 4 carbon atoms and the corresponding mono- or di-$(C_1-C_2)$alkyl ethers or esters, e.g., ethylene glycol, ethylene glycol monomethyl or monoethyl ether, ethyleneglycol monoisopropyl ether, ethylene glycol monoacetate; 1,2-propanediol, 1,3-propanediol, 1,3-propanediol monoacetate; 1,3-propanediol monoethyl ether, 1,2-butanediol, 2,3-butanediol or 2,3-butanediol monomethyl ether, benzyl alcohol.

According to a preferred embodiment of the present invention a large excess of the suitably selected amine of formula $R^5R^6NH$ is employed to act as the reactant as well as the solvent in this reaction step. In any case, the reaction mixture is heated between about 85° C. and the reflux temperature. The reaction time depends on the particular reactants and reaction conditions employed, however the reaction is generally complete in about 2-12 hours. Then water is added while keeping the temperature above 85° C. The solid that separates is the derivative of formula I, which is recovered through common procedures.

Sometimes this reaction step is carried out in autoclave or in Parr bombs, so that a higher pressure and temperature can be reached. The pressure is generally increased freely, the upper limit being the pressure that the apparatus can safely bear, while the temperature is preferably kept between 140° C. and 200° C., even if lower temperatures can be used.

As states above, the overall yields of the process are always higher than 30%, and often are 50-70%, while the yields of the prior-art processes, starting from the same 3,6-dihalogen pyridazine derivative range between 5% and 30%. Therefore, the advantage of the present invention is apparent.

The intermediates of formula V and VI were not previously described in the chemical literature and represent a further object of the present invention.

The following examples illustrate the manner in which those skilled in the art can practice the invention but should not be construed as imposing any limitations upon the overall scope of the same.

EXAMPLE 1

N-(2,5-dimethyl-1H-pyrrol-1-yl)-6-(4-morpholinyl)-3-pyridazineamine (A) A suspension of 3,6-dichloropyridazine (660 g; 4.4 mole), 98% hydrazine hydrate (226 g; 4.4 mole) and sodium bicarbonate (375 g; 4.6 mole) in water (1800 ml), is heated to reflux temperature, under stirring, for 2 hours. Then ethanol (100 ml) is slowly added and reflux is prolonged for additional 3 hours. Water (1000 ml), is added and, keeping the temperature over 60° C., acetonylacetone (317 g, 2.78 mole) is, in turn, added. The temperature rises and a pale yellow precipitate forms. The suspension is neutralized with 17% hydrochloric acid; after filtration the collected insoluble material is washed with water until chloride ions are absent in the filtrate. The product is dried in vacuo at 50° C.–60° C. Yield 756 g (93%). M.p. 200°–202° C.

The structure of the obtained 2,5-hexanedione-bis-(6-chloro-3-pyridazinyl)-hydrazone is confirmed by the I.R. and N.M.R. spectra.

(B) The product of the above reaction (587 g; 1.6 mole), is slowly added to acetic acid (500 ml) and acetonylacetone (183 g; 1.6 mole), while heating to 90°–110° C. Once the addition is completed, a precipitate separates; the collected solid is washed with 50% cold acetic acid in water and dried in vacuo, yielding 557 g (78%) of 6-chloro-N-(2,5-dimethyl-1H-pyrrol-1-yl)-3-pyridazineamine. M.p. 173°–175° C.

(C) A mixture of the above product (89 g; 0.4 mole), morpholine hydrochloride (0.5 g; 0.005 mole), and morpholine (150 ml; 1.72 mole), is heated to the reflux temperature for 3 hours. Water is added while keeping the temperature above 85° C., and the obtained suspension is stirred for 1 hour, then filtered. The collected insoluble material is washed with water and dried in vacuo to yield 106 g of crude material. Crystallization from isopropanol yields 96 g (88%) in the product of the title. M.p. 190°–192° C.

The hydrochloride of the above product is described in Example 3 of the European Patent Application Publication No. 9655.

Following the process of the said application and preparing the starting 6-hydrazino-3-morpholino-pyridazine according to U.K. Pat. No. 1,157,642, the product of the title is obtained with a yield of about 25%, while the present process yields 65%, starting from the same 3,6-dihalogenpyridazine.

EXAMPLE 2

N-(2,5-dimethyl-1H-pyrrol-1-yl)-6-(N,N-diethylamino)-pyridazine, hydrochloride.

(C) 3-Chloro-(2,5-dimethyl-1H-pyrrol-1-yl)-pyridazine (40 g; 0.18 mole) obtained essentially following points A and B of example 1, diethylamine hydrochloride (4 g), and diethylamine (92 g; 0.126 mole) are heated at 160°–170° C. in a Parr bomb, under stirring for 14 hours reaching 12 atm. pressure. After distillation in vacuo of the solvent, the residue is dissolved in boiling ethyl ether (2000 ml) and then hydrogen chloride is bubbled into the solution. The obtained precipitate is collected and dried yielding 44 g of the crude product of the title. Crystallization by acetonitrile yields 27.2 g (51%). M.p. 168° C.

The prior-art processes, according to European Patent Application Publication No. 9655 and Pifferi et al. (quoted paper), yield 6% in the product of the title, while the present process, yields 36% starting from the same 3,6-dichloropyridazine derivative.

EXAMPLE 3

N-(2,5-dimethyl-1H-pyrrol-1-yl)-N-methyl-6-(4-morpholinyl)-3-pyridazineamine (A) A mixture of water (300 ml), 3,6-dichloropyridazine (29.8 g; 0.2 mole), methylhydrazine (9.2 g; 0.2 mole), and sodium bicarbonate (17.8 g; 0.2 mole), is heated to the reflux temperature for two hours. After cooling to about 60° C., acetonylacetone (22.2 g; 0.2 mole) is added and stirring is prosecuted for further 1 hour. Then the mixture is neutralized with hydrochloric acid and the obtained precipitate is collected and crystallized from ethyl ether, yielding 28 g (59.2%) of 6-chloro-N-(2,5-dimethyl-1H-pyrrol-1-yl)-N-methyl-3-pyridazineamine, whose structure is confirmed by I.R. and NMR spectra. M.p. 93°–94.5° C.

(B) The above product (10 g; 0.042 mole) is dissolved in morpholine (70 ml; 0.86 mole) and heated to the reflux temperature for about 6 hours. Then the reaction mixture is concentrated to dryness in vacuo, the residue is taken up with water and filtered. The collected solid is washed thoroughly and crystallized from a mixture hexane/t-butyl ether, yielding 10.5 g (82%) of the product of the title. M.p. 119°–122° C.

The overall yield is therefore about 40%, while according to the prior-art methods (European Patent Application Publication No. 9655 and U.K. Pat. No. 1,157,642), a yield of about 13% is obtained, starting from the same 3,6-dichloropyridazine.

EXAMPLE 4

Isolation of the intermediate 6-chloro-3-(methylhydrazine)-pyridazine.

A mixture of water 3,6-dichloropyridazine, methylhydrazine and sodium bicarbonate is refluxed for two hours and then cooled to room temperature. The solid is collected and identified as the product of the title. M.p. 104°–106° C. I.R. and N.M.R. spectra confirmed the structure.

I claim:

1. A process for preparing N-pyrrolyl pyridazineamines and their acid addition salts having the formula

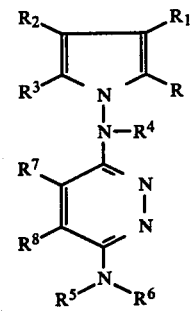

wherein R, $R^1$, $R^2$ and $R^3$ may be the same or different and are independently selected from hydrogen and $(C_1-C_4)$alkyl, $R^4$ represents hydrogen, $(C_1-C_4)$alkyl, mono- or di-$(C_1-C_4)$-alkylamino$(C_1-C_4)$alkyl, halo$(C_1-C_4)$alkanoyl, carbo $(C_1-C_4)$-alkoxy, carbobenzyloxy, $R^5$ and $R^6$ independently represent hydrogen, $(C_1-C_6)$alkyl, $(C_3-C_6)$alkenyl, $(C_3-C_6)$alkynyl, hydroxy$(C_1-C_6)$alkyl, $(C_1-C_4)$alkoxy$(C_1-C_6)$alkyl, $(C_2-C_6)$-alkanoyloxy$(C_1-C_6)$alkyl, phenyl or phenyl$(C_1-C_4)$alkyl, wherein the phenyl group may be optionally substituted with from 1 to 3 substituents independently selected from chloro, bromo, fluoro, $(C_1-C_4)$alkyl, $(C_1-C_4)$alkoxy, hydroxy and hydroxy$(C_1-C_4)$alkyl, or with a methylenedioxy group, or $R^5$ and $R^6$ taken together with the adjacent nitrogen atom represent a wholly or partially hydrogenated 5-7 membered heterocyclic ring, which may contain a further heteroatom selected from O, N, and S and which may optionally bear from 1 to 2 substituents selected from $(C_1-C_4)$alkyl, hydroxy, hydroxy$(C_1-C_4)$alkyl, $(C_1-C_4)$alkoxy, or phenyl which may be optionally substituted as above, $R^7$ and $R^8$ represent hydrogen atoms or when taken together, a 1,3-butadienylene group forming a benzo system fused with the pyridazine ring, which is characterized by:

(a) reacting an appropriately substituted 3,6-dihalopyridazine with hydrazine hydrate or a suitable hydrazine derivative having the formula $NH_2NH-R^4$ wherein $R^4$ is as indicated above, preferably in the presence of a hydrogen halide acceptor;

(b) reacting the 6-halo-3-hydrazinopyridazine derivative so obtained with about a half molar amount of a dicarbonyl compound having the formula

wherein R, $R^1$, $R^2$ and $R^3$ are as indicated above;

(c) treating the alkanedione-bis-[6-halo-3-pyridazinyl]-hydrazone so obtained with about an equimolar amount of the aforementioned dicarbonyl compound preferably in the presence of an acid catalyst and a solvent;

(d) reacting the 6-halo-N-pyrrolyl-3-pyridazineamine so obtained with an excess of an amine having the formula $R^5R^6NH$ wherein $R^5$ and $R^6$ are as indicated above, optionally in the presence of a suitable acid catalyst; and (e) isolating the desired N-pyrrolyl pyridazineamine therefrom.

2. A process as in claim 1 for preparing a compound of formula I wherein $R^1$ and $R^2$ represent hydrogen, R and $R^3$ may be the same or different and represent $(C_1-C_4)$alkyl, $R^5$ and $R^6$ each independently represent $(C_1-C_6)$alkyl, hydroxy$(C_1-C_6)$alkyl or $(C_1-C_4)$alkoxy$(C_1-C_6)$alkyl, or $R^5$ and $R^6$ taken together with the adjacent nitrogen atom represent a 5-7 membered heterocyclic ring which may contain a further heteroatom selected from O, N, and S, and bear 1 or 2 substituents selected from $(C_1-C_4)$alkyl, hydroxy, hydroxy$(C_1-C_4)$alkyl and phenyl optionally substituted with 1 to 3 substituents independently selected from chloro, fluoro, bromo, hydroxy$(C_1-C_4)$alkyl and $(C_1-C_4)$alkoxy.

3. A process as in claim 1 or 2 wherein the reaction between the 3,6-dihalogen pyridazine and hydrazine hydrate or the hydrazine hydrate derivative, is carried out in an autoclave or Parr bomb, preferably heating to 100°–190° C.

4. A process as in claims 1 or 2, wherein a molar excess of the dicarbonyl compound is added to the 6-halo-3-hydrazino derivative to obtain directly the derivative of 6-halo-N-pyrrolyl-3-pyridazine amine.

5. A process as in claims 1 or 2 inclusive, wherein the suitable solvent for the reaction of the alkandione-bis-6-halogen-3-pyridazinyl hydrazone with the dicarbonyl compound is selected from water, $(C_1-C_4)$alkanols, acetic or propionic acid, benzene, toluene, tetrahydrofuran, dioxane and mixture thereof, and the acid catalyst is selected from hydrohalidic acids, sulphuric acid, p-toluenesulfonic acid and Lewis acids.

6. A process as in any one of claims 1 or 2, further characterized in that acetic acid is used to act both as the solvent and the catalyst.

7. A process as in claims 1 or 2, wherein the addition of the amine of formula $R^5R^6NH$ is carried out in the presence of an acid addition salt of the amine, which acts as the acidic catalyst.

8. A process as in claim 1 for preparing N-(2,5-dimethyl-1H-pyrrol-1-yl)-6-(4-morpholinyl)-3-pyridazineamine.

9. A process according to claim 1 wherein the addition of the 6-halo-3-hydrazinopyridazine derivative with about a half molecular proportion of the dicarbonyl compound is carried out in an aqueous medium.

* * * * *

UNITED STATES PATENT AND TRADEMARK OFFICE
CERTIFICATE OF CORRECTION

PATENT NO. : 4,385,179

DATED : May 24, 1983

INVENTOR(S) : Elvio Bellasio

It is certified that error appears in the above-identified patent and that said Letters Patent are hereby corrected as shown below:

At Column 10, Line 25, patent reads "hydrazino derivative" and should read --hydrazino pyridazine derivative--.

Signed and Sealed this

Fourteenth Day of March, 1989

Attest:

DONALD J. QUIGG

*Attesting Officer*  *Commissioner of Patents and Trademarks*